United States Patent
Stojadinovic et al.

(10) Patent No.: US 12,248,110 B1
(45) Date of Patent: Mar. 11, 2025

(54) SYSTEM AND METHOD FOR RADIOCHROMIC FILM CALIBRATION UTILIZING NON-IONIZING RADIATION

(71) Applicants: Strahinja Stojadinovic, Dallas, TX (US); Stevan Pecic, Trstenik (RS)

(72) Inventors: Strahinja Stojadinovic, Dallas, TX (US); Stevan Pecic, Trstenik (RS)

( * ) Notice: Subject to any disclaimer, the term of this patent is extended or adjusted under 35 U.S.C. 154(b) by 0 days.

(21) Appl. No.: 18/944,285

(22) Filed: Nov. 12, 2024

Related U.S. Application Data

(60) Provisional application No. 63/660,789, filed on Jun. 17, 2024.

(51) Int. Cl.
*G01T 7/00* (2006.01)
*A61N 5/10* (2006.01)
*G01T 1/08* (2006.01)

(52) U.S. Cl.
CPC .............. *G01T 7/005* (2013.01); *G01T 1/08* (2013.01); *A61N 5/1071* (2013.01)

(58) Field of Classification Search
CPC .................................. G01T 7/005; G01T 1/08
See application file for complete search history.

(56) References Cited

U.S. PATENT DOCUMENTS

| | | | |
|---|---|---|---|
| 4,820,922 A | 4/1989 | Nakajima | |
| 4,886,968 A | 12/1989 | Ohnishi | |
| 5,012,095 A | 4/1991 | Horikawa | |
| 6,163,339 A | 12/2000 | Meunier | |
| 6,528,803 B1 | 3/2003 | Ritt | |
| 6,927,859 B2 * | 8/2005 | Kwok | G01N 21/5911 356/443 |
| 7,405,412 B2 | 7/2008 | Lewis | |
| 8,399,858 B2 | 3/2013 | Yoder | |
| 8,894,280 B2 | 11/2014 | Topfer | |
| 11,726,217 B2 | 8/2023 | De Jean | |

(Continued)

FOREIGN PATENT DOCUMENTS

CN 106137242 B 2/2020

OTHER PUBLICATIONS

Penner, C.; Usherovich, S.; Andru, S.; Belanger-Champagne, C.; Duzenli, C.; Stoeber, B.; Hoehr, C. A Multi-Point Optical Fibre Sensor for Proton Therapy. Electronics 2024, 13, 1118. https://doi.org/10.3390/ electronics13061118.

(Continued)

*Primary Examiner* — Dani Fox
*Assistant Examiner* — Casey Bryant
(74) *Attorney, Agent, or Firm* — Peacock Law Firm PLLC; Aaron P. Peacock

(57) ABSTRACT

A system and method for radiochromic film calibration utilizing non-ionizing radiation to achieve controlled and reproducible exposures without the need for ionizing radiation sources or specialized expertise. The system includes a non-ionizing photon source, such as LEDs or laser diodes, emitting ultraviolet or visible light, a mechanical shutter to control exposure duration, and a control unit regulating light emission and shutter operation. A variable optical element of a collimator can be used to shape and direct the light beam for uniform exposure. Precise calibration of the system is performed through a field radiometer for routine verification and periodic cross-validation with ionizing radiation sources.

9 Claims, 6 Drawing Sheets

(56) References Cited

U.S. PATENT DOCUMENTS

2015/0246336 A1    9/2015   Somoza

OTHER PUBLICATIONS

Cho, C.; Son, J.; Choi, C.; Kim, J.; Wu, H.; Park, J.; Kim, J. Improvement In Sensitivity of Radiochromic 3D Dosimeter Based on Rigid Polyurethane Resin by Incorporating Tartrazine. Plos One 2020. https://www.ncbi.nlm.nih.gov/pmc/articles/PMC7075553/.
Skanray Technologies PVT. Ltd., X-Ray Collimator Mechanism with Precision Aperture Adjustment. Sep. 20, 2014.
Chun, S. L.; Yu, P. K. N. Note: Calibration of EBT3 Radiochromic Film for Measuring Solar Ultraviolet Radiation. Rev. Sci. Instrum. 85, 106103 (2014), https://doi.org/10.1063/1.4898162.
Butson, Martin J.; Cheung, Tsang; Yu, Peter K.N.; Abbati, Donna; Greenoak, Gavin E. Ultraviolet Radiation Dosimetry with Radiochromic Film. 2000 Phys. Med. Biol. 45 1863, https://iopscience.iop.org/article/10.1088/0031-9155/45/7/311.

* cited by examiner

Wedge field calibration procedure

SYSTEM AND METHOD FOR RADIOCHROMIC FILM CALIBRATION UTILIZING NON-IONIZING RADIATION

BACKGROUND

1. Field of the Invention

The present invention relates generally to systems and methods for radiochromic film calibration utilizing non-ionizing radiation.

2. Description of Related Art

The electromagnetic spectrum encompasses a broad range of radiation, including gamma rays, X-rays, ultraviolet light, visible light, infrared light, microwaves, and radio waves. These diverse forms of electromagnetic radiation play a fundamental role in numerous applications that underpin modern society, from electronics and communication technologies to medical diagnosis and treatment. X-ray imaging, for instance, utilizes the penetrating power of X-rays to visualize internal structures, while radiotherapy leverages the targeted destructive properties of ionizing radiation to treat cancer.

One valuable device or a dosimeter for measuring radiation dose is the radiochromic film. However, current radiochromic film calibration methods employed in both medical physics and industrial settings often necessitate highly trained personnel, expensive ionizing radiation sources, and time-consuming manual procedures. Consequently, the widespread adoption of radiochromic films is hindered by the significant technical costs associated with both ionizing radiation and the specialized expertise required for pre-use calibration.

This patent proposes a novel approach for calibrating radiochromic films using standardized non-ionizing light-emitting elements. This innovative method has the potential to streamline the calibration process, making it more efficient and reliable. By eliminating the need for expensive ionizing radiation sources and specialized expertise, this approach could significantly broaden the applicability of radiochromic films in radiotherapy and various industrial applications.

Accordingly, although great strides have been made in the area of radiochromic film calibration, many shortcomings remain. A novel method for radiochromic film calibration using non-ionizing radiation presents a compelling alternative by eliminating the intricate prerequisites associated with traditional ionizing radiation methods. This innovative approach offers distinct advantages, including enhanced safety, operational simplicity, and broader applicability.

DESCRIPTION OF THE DRAWINGS

The appended claims set forth the novel features believed characteristic of the embodiments of the present application. However, the embodiments themselves, as well as a preferred mode of use, and further objectives and advantages thereof, will best be understood by reference to the following detailed description when read in conjunction with the accompanying drawings, wherein:

Figure 1:
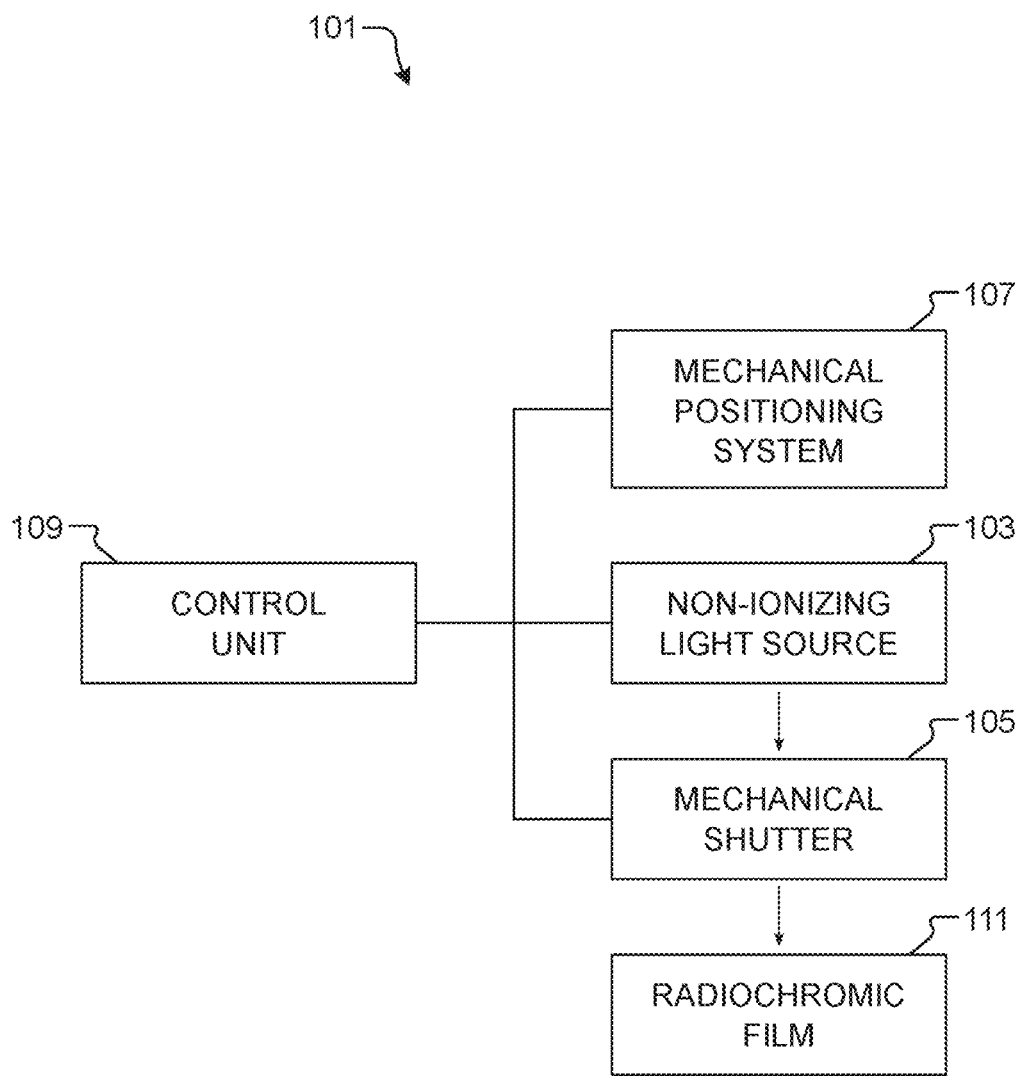
FIG. 1 is simplified schematic diagram of an irradiation apparatus in accordance with a preferred embodiment of the present invention.
Figure 2:
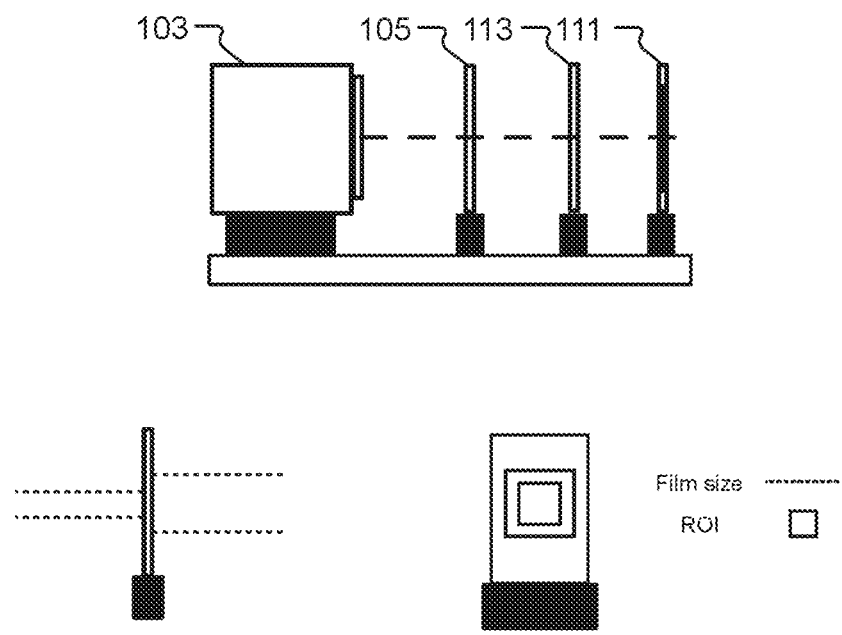
FIG. 2 is simplified view of an irradiation apparatus in accordance with a preferred embodiment of the present invention.
Figure 3A:
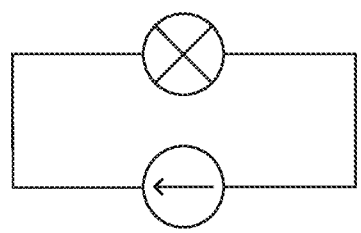
FIG. 3A is simplified view of current regulation of the light source in accordance with a preferred embodiment of the present invention.
Figure 3B:
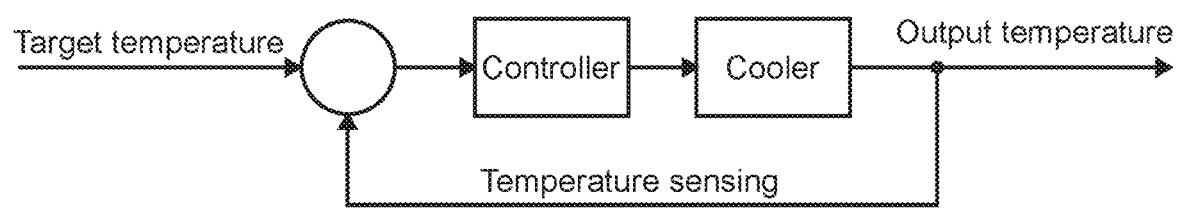
FIG. 3B is simplified view of temperature regulation of the light source in accordance with a preferred embodiment of the present invention.
Figure 4A:
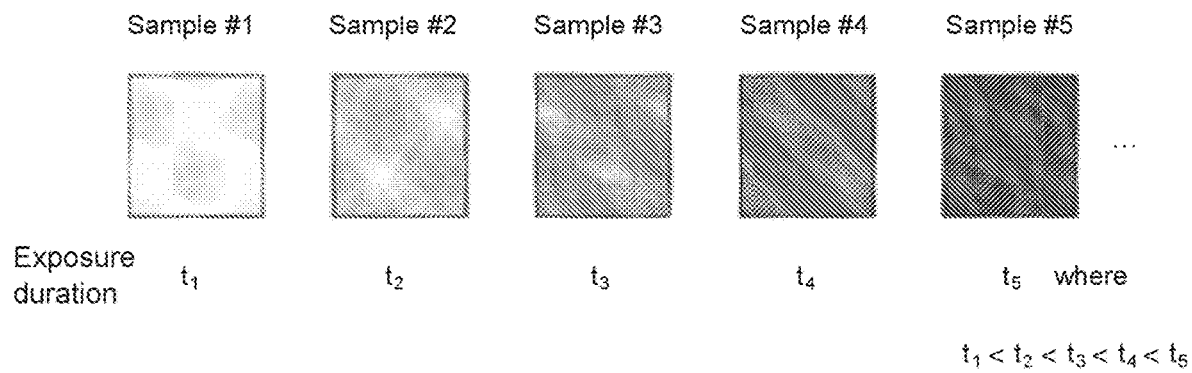
FIG. 4A is simplified view of a uniform field calibration procedure in accordance with a preferred embodiment of the present invention.
Figure 4B:
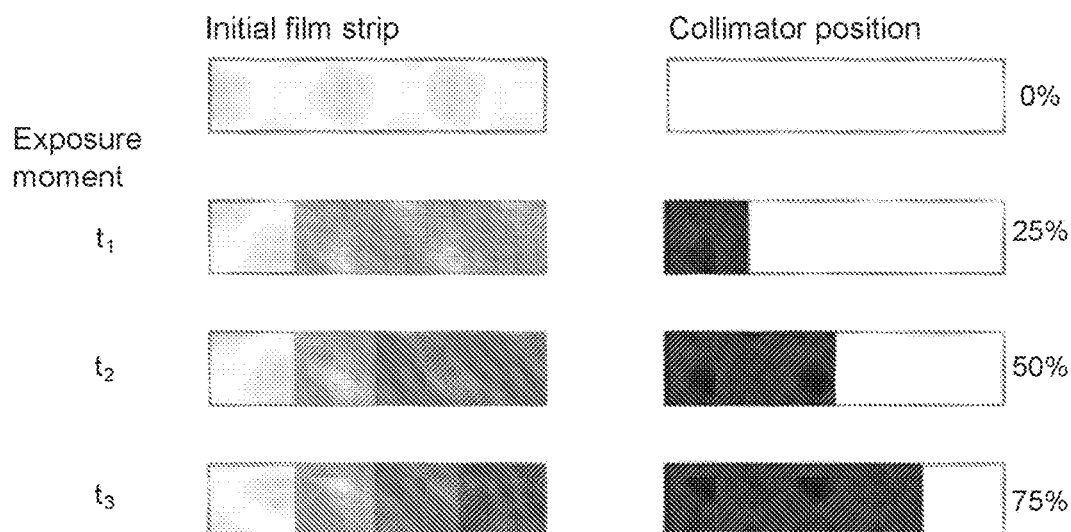
FIG. 4B is simplified view of a wedge field calibration procedure in accordance with a preferred embodiment of the present invention.

While the system and method of use of the present application are susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcome one or more of the above-discussed problems commonly associated with conventional radiochromic film calibration methods. Specifically, the system of the present invention utilizes non-ionizing radiation, such as ultraviolet (UV) or visible light, to achieve controlled and reproducible exposures, eliminating the need for expensive ionizing radiation sources and specialized expertise. These and other unique features of the system and method of use are discussed below and illustrated in the accompanying drawings.

The system and method of use will be understood, both as to its structure and operation, from the accompanying drawings, taken in conjunction with the accompanying description. Several embodiments of the device are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments are expressly contemplated herein so that one of ordinary skill in the art would appreciate from this disclosure that the features, elements, and/or functions of one embodiment may be incorporated into another embodiment as appropriate unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

The present disclosure details a system and method for radiochromic film calibration that capitalizes on the intrinsic sensitivity of these films to UV and visible light for achieving controlled and reproducible exposures. The method employs a dedicated light source capable of inducing a measurable darkening response within seconds. This innovation streamlines the calibration process, leading to significant improvements in both efficiency and accuracy.

Referring now to the drawings wherein like reference characters identify corresponding or similar elements throughout the several views, FIGS. 1-4 depict various diagrams for a system 101 for radiochromic film calibration and methods thereof in accordance with a preferred embodiment of the present application. It will be appreciated that the system 101 and method overcome one or more of the above-listed problems commonly associated with conventional calibration methods. In addition, it should be appreciated that more or fewer of such components may be included in different embodiments of the system 101 and method.

In the contemplated embodiment, the system 101 for calibrating radiochromic films includes a non-ionizing photon source 103, or light source, configured to emit ultraviolet or visible light, a mechanical shutter 105 positioned to control the exposure of a radiochromic film 111 to the light emitted by the non-ionizing photon source 103, and a control unit 109 operatively connected to the non-ionizing photon source 103 and the mechanical shutter 105. The control unit 109 is configured to regulate the emission of light from the non-ionizing photon source 103 and to control the operation of the mechanical shutter 105 to achieve a predetermined exposure duration. The light source 103 is further integrated with a mechanical positioning system 107 to facilitate precise adjustment for varying film dimensions and source-to-film distances.

In various embodiments, the light source 103 assembly preferably utilizes high-power light emitters, such as the light-emitting diodes (LEDs) or laser diodes that generate controllable radiation within the ultraviolet (UV) or visible wavelength range, or any other suitable photon-emitting element or combinations thereof. The use of non-ionizing radiation enables radiometric calibration traceable to national standards upheld by accredited dosimetry laboratories, or by a primary standard laboratory, such as the National Institute of Standards and Technology (NIST). Notably, both UV and visible wavelengths induce rapid coloration or darkening of reference calibration films. Consequently, the selection of UV or visible wavelengths necessitates the implementation of distinct specialized components for advanced stabilization and regulation mechanisms within the calibration setups. The housing integrates control system 101s for precise adjustment of the emitted light's intensity.

To ensure the appropriate flux of incident light, the radiochromic film is positioned close to the light source 103.

The mechanical shutter 105 is positioned between the non-ionizing photon source 103 and the radiochromic film 111, configured to control the exposure duration of the film 111 to the light emitted by the non-ionizing photon source 103.

The control unit 109 is operatively connected to the light source 103 and the mechanical shutter 105. The control unit 109 is configured to precisely trigger the mechanical shutter 105 for a pre-defined exposure time, and is further configured to regulate operating parameters of the light source 103, such as, but not limited to, emitter temperature and current. The system 101 operates in a constant light output mode, utilizing the mechanically actuated shutter 105 to control exposure duration. This approach ensures stability and repeatability of both spectrum and intensity within a single exposure and across subsequent exposures.

It is also contemplated and will be appreciated that the system 101 can incorporate a variable optical element or a collimator 113 positioned between the non-ionizing photon source 103 and the radiochromic film 111. The collimator 113 is configured to shape and direct the light beam onto the radiochromic film 111, ensuring uniform exposure across the film 111. The collimator may be used to achieve specific calibration requirements and enhance the precision of the calibration process.

Preferably, a radiometer calibrated for the relevant wavelength range is employed for routine verification of the light source's output power. This verification is necessary due to potential variations arising from inherent uncertainties in environmental measurement conditions and the inevitable aging effects on the light sources.

To ensure the integrity of the radiometric non-ionizing calibration, periodic verification procedures can be implemented utilizing a dedicated ionizing radiation source, such as a linear accelerator or a Cobalt-60 source. This approach facilitates independent cross-validation of the accuracy of both ionizing and non-ionizing calibrations. Notably, this method offers a novel scientific technique currently unavailable within the scientific community. The degree of coloration or darkening induced in calibration films by both ionizing and non-ionizing radiation exposure can be quantitatively compared using a densitometer. Transmission mode densitometers measure the amount of light that is transmitted through a transparent or translucent material, such as film or a photographic negative.

Figure 5:
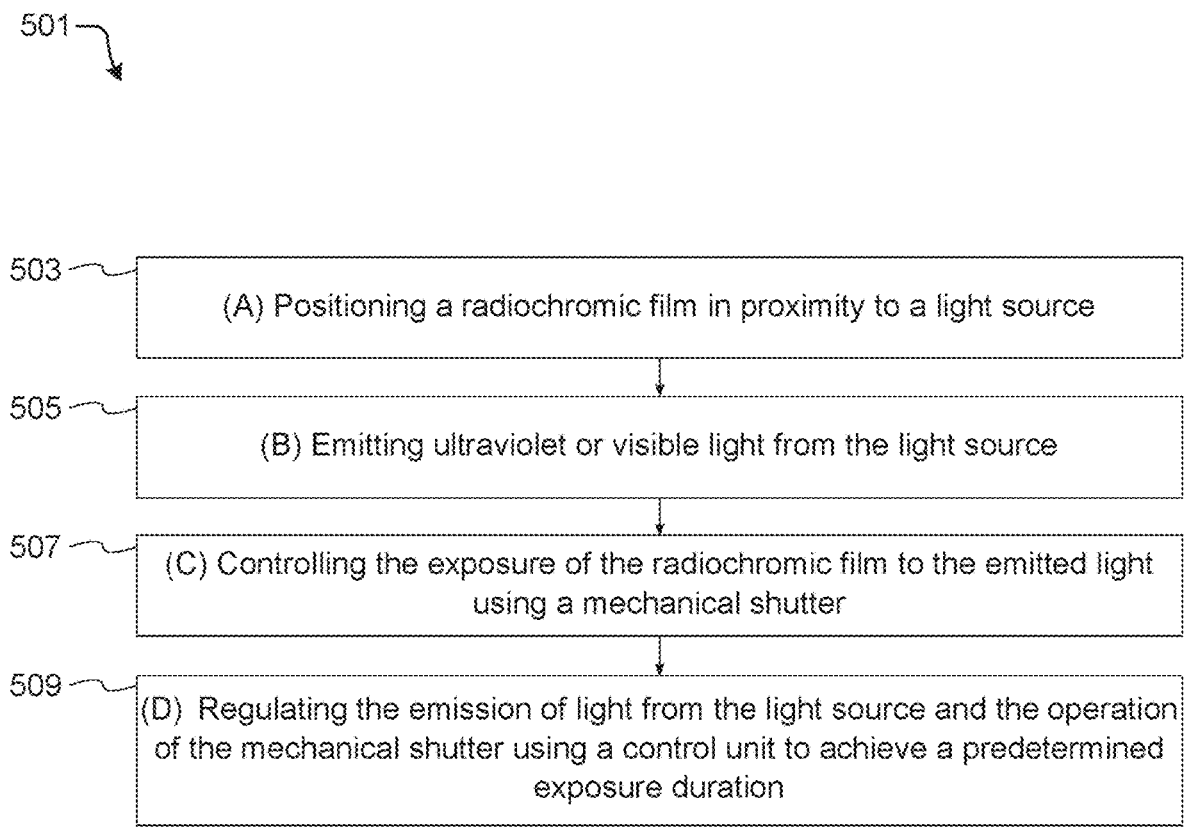
FIG. 5 is a flowchart of a simplified method of use in accordance with a preferred embodiment of the present invention.
Figure 6:
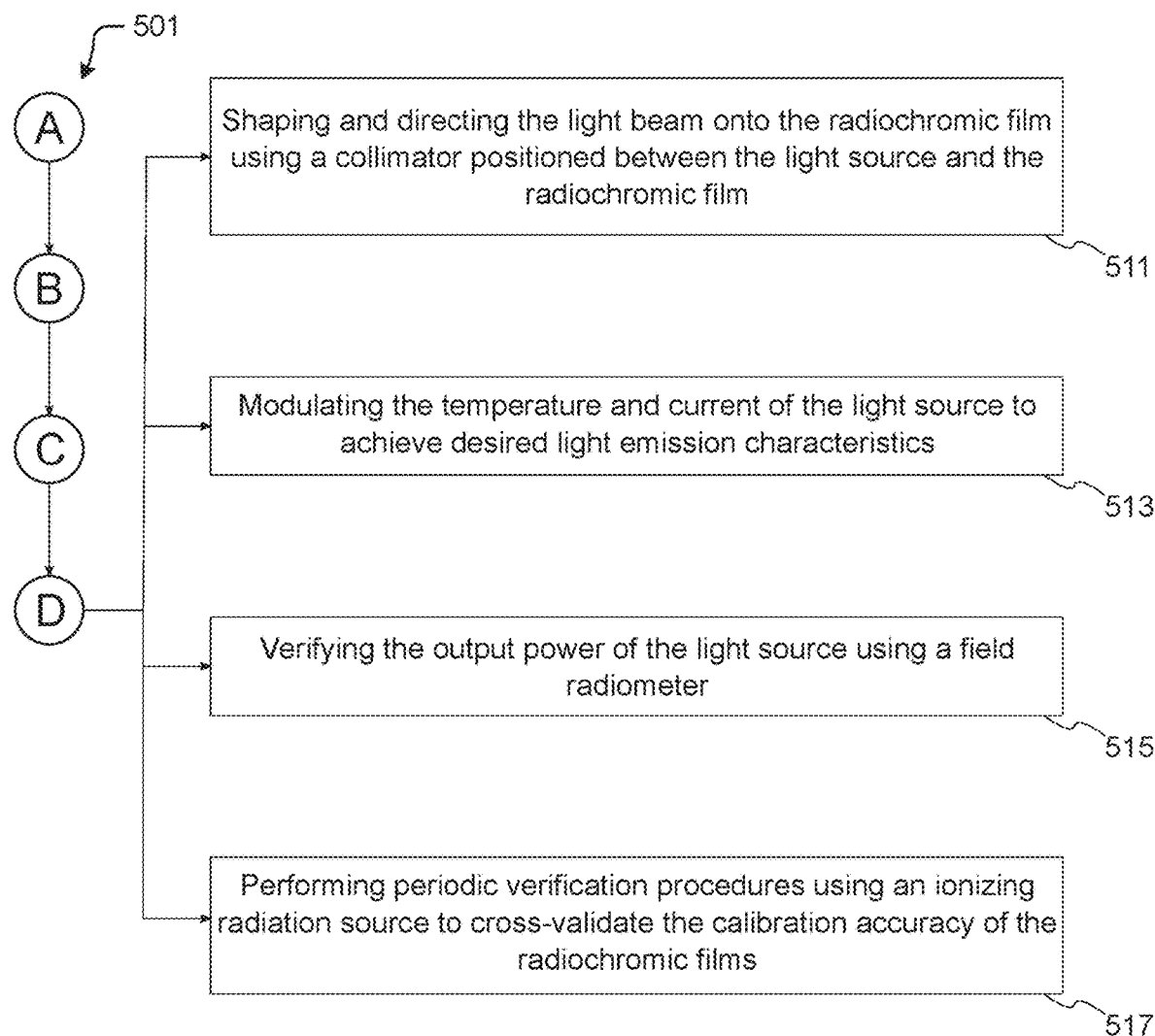
FIG. 6 is a continuation of FIG. 5.

FIG. 5 depicts a simplified method of use 501 associated with the system of FIGS. 1-4 in accordance with an embodiment of the present invention. The method 501 initiates with step 503 of positioning a radiochromic film in proximity to a non-ionizing light source. The method further includes emitting ultraviolet or visible light from the non-ionizing light source 505 and controlling the exposure of the radiochromic film to the emitted light using a mechanical shutter 507. The emission of light from the non-ionizing photon source is regulated and the operation of the mechanical shutter using a control unit to achieve a predetermined exposure duration 509.

The method may also include shaping and directing the light beam onto the radiochromic film using a variable optical element or a collimator positioned between the non-ionizing photon source and the radiochromic film 511, modulating the temperature and current of the non-ionizing photon source to achieve desired light emission characteristics 513, verifying the output power of the non-ionizing photon source using a field radiometer 515, and performing periodic verification procedures using an ionizing radiation source to cross-validate the calibration accuracy of the radiochromic films 517.

Advantages of the present invention include: (1) Enhanced Calibration Efficiency: This innovative solution streamlines the calibration process, resulting in significant reductions in both time and labor requirements. (2) Metrology: Rigorous control and repeatability of exposure are paramount in metrology, minimizing errors and ensuring precise calibration. (3) Safety: Leveraging the inherent safety of non-ionizing radiation, this system offers a compact and user-friendly design with simplified maintenance.

The present invention represents a paradigm shift in radiochromic film calibration. It capitalizes on the films' inherent sensitivity to ultraviolet and visible light for radiometric non-ionizing calibrations. This innovative approach eliminates the high cost barriers associated with traditional ionizing radiation methods, resulting in a significantly more efficient and cost-effective calibration solutions.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments but are amenable to various changes and modifications without departing from the spirit thereof.

What is claimed is:

1. A system for calibrating radiochromic films, comprising:
    a light source configured to emit non-ionizing radiation as ultraviolet or visible light;
    a mechanical positioning system integrated with the light source configured to facilitate precise position and orientation adjustment of the light source;
    a mechanical shutter positioned to control the exposure of a radiochromic film to the light emitted by the light source; and
    a control unit operatively connected to the light source and the mechanical shutter, the control unit configured to regulate the emission of light from the light source and to control the operation of the mechanical shutter to achieve a predetermined exposure duration.

2. The system of claim 1, further comprising a variable optical element or a collimator positioned between the light source and the radiochromic film, the collimator configured to shape and direct the light beam onto the radiochromic film.

3. The system of claim 1, wherein the light source comprises a light-emitting diode (LED) or a laser diode.

4. The system of claim 1, wherein the control unit is configured to modulate the temperature and current of the light source to achieve desired light emission characteristics.

5. A method for calibrating radiochromic films, the method comprising the steps of:
    (A) positioning a radiochromic film in proximity to a light source;
    (B) emitting non-ionizing ultraviolet or visible light from the light source;
    (C) controlling the exposure of the radiochromic film to the emitted light using a mechanical shutter; and
    (D) regulating the emission of light from the light source and the operation of the mechanical shutter using a control unit to achieve a predetermined exposure duration.

6. The method of claim 5, further comprising shaping and directing the light beam onto the radiochromic film using a variable optical element or a collimator positioned between the light source and the radiochromic film.

7. The method of claim 6, further comprising modulating the temperature and current of the light source to achieve desired light emission characteristics.

8. The method of claim 6, further comprising verifying the output power of the light source using a radiometer.

9. The method of claim 6, further comprising performing periodic verification procedures using an ionizing radiation source to cross-validate the calibration accuracy of the radiochromic films.

* * * * *